(12) United States Patent
Baumgartner

(10) Patent No.: US 10,133,412 B2
(45) Date of Patent: Nov. 20, 2018

(54) INTUITIVE TOUCH SCREEN CALIBRATION DEVICE AND METHOD

(71) Applicant: General Electric Company, Schenectady, NY (US)

(72) Inventor: Claus Christer Baumgartner, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 92 days.

(21) Appl. No.: 14/508,549

(22) Filed: Oct. 7, 2014

(65) Prior Publication Data

US 2016/0098149 A1 Apr. 7, 2016

(51) Int. Cl.
*G06F 3/041* (2006.01)
*G06F 3/0488* (2013.01)

(52) U.S. Cl.
CPC ............ *G06F 3/0418* (2013.01); *G06F 3/041* (2013.01); *G06F 3/04883* (2013.01); *A61M 2205/505* (2013.01)

(58) Field of Classification Search
CPC ......... G09G 5/00; G06F 3/0418; G06F 3/043; G06F 3/0433; G06F 3/0436; G06F 2203/041; G06F 3/03547; G06F 3/041; G06F 3/0412; G06F 3/0414; G06F 3/0416; G06F 3/046; G06F 3/047; G06F 3/04883; H05K 9/0073; H05K 9/0079; H05K 9/0081; A61M 2205/505
USPC .................................................. 345/156–178
See application file for complete search history.

(56) References Cited

U.S. PATENT DOCUMENTS

| | | | | |
|---|---|---|---|---|
| 4,710,758 A | * | 12/1987 | Mussler | G06F 3/0418 340/571 |
| 4,903,012 A | * | 2/1990 | Ohuchi | G06F 3/0418 345/178 |
| 5,471,226 A | * | 11/1995 | Suzuki | G06F 3/0418 178/18.02 |
| 5,751,276 A | * | 5/1998 | Shih | G06F 3/0418 345/178 |
| 5,804,773 A | * | 9/1998 | Wilson | G06F 3/045 178/18.05 |
| 6,086,236 A | * | 7/2000 | De Raad | G06F 3/038 700/275 |
| 6,181,328 B1 | * | 1/2001 | Shieh | G06F 3/0418 345/173 |
| 6,353,434 B1 | * | 3/2002 | Akebi | G06F 3/0418 345/173 |
| 6,507,339 B1 | * | 1/2003 | Tanaka | G06F 3/0418 345/175 |
| 7,081,886 B2 | * | 7/2006 | Nakano | G06F 3/0418 345/173 |
| 7,327,353 B2 | * | 2/2008 | Wang | G06F 3/0418 345/173 |
| 2002/0070926 A1 | * | 6/2002 | Kavanagh | G06F 3/0418 345/173 |

(Continued)

*Primary Examiner* — Grant Sitta

(57) ABSTRACT

In the present invention a touch screen display optionally connected to a piece of monitoring equipment is configured with a calibration procedure that can be initiated directly through the screen of the touch screen display by the operator performing a predetermined pattern of points of contact with the screen. The calibration procedure uses the pattern of points of contact with the screen to calibrate the touch screen display, as well as to initiate the procedure.

10 Claims, 2 Drawing Sheets

(56) References Cited

U.S. PATENT DOCUMENTS

| | | | |
|---|---|---|---|
| 2008/0150909 A1* | 6/2008 | North | G06F 3/0418 345/173 |
| 2009/0109195 A1* | 4/2009 | Kent | G06F 3/045 345/178 |
| 2009/0315838 A1* | 12/2009 | Geiger | G06F 3/0418 345/173 |
| 2010/0321307 A1* | 12/2010 | Hirokawa | G06F 3/0418 345/173 |
| 2012/0287087 A1* | 11/2012 | Lu | G06F 3/0418 345/178 |
| 2013/0127980 A1* | 5/2013 | Haddick | G06F 3/013 348/14.08 |
| 2013/0162603 A1* | 6/2013 | Peng | G06F 3/0418 345/178 |
| 2015/0324041 A1* | 11/2015 | Varley | G06F 3/0412 345/173 |

* cited by examiner

INTUITIVE TOUCH SCREEN CALIBRATION DEVICE AND METHOD

BACKGROUND OF THE INVENTION

The invention relates generally to touch screen displays, and more particularly to methods for calibration of touch screens or touch screen displays.

Touch screens or touch screen displays, including all types of devices that can be operated by individuals contacting touch-sensitive screens located on the device, are often utilized as controls for the operation of various types of equipment and/or as displays for information from the equipment. These screens are connected to the various pieces of equipment and then calibrated in order to provide the appropriate display to in the operator for the efficient and effective use of the screen to control the equipment and view the operating parameters of the equipment.

When connected to the equipment, in order to calibrate the touch screen during the start-up of the equipment and/or the touch screen, initially an operator must often connect a separate, secondary device, such as a mouse or keyboard to the device and/or screen in order to run the appropriate calibration program necessary to calibrate the touch screen for proper operation of the equipment. Once calibrated, the secondary device can be disconnected and the touch screen can be utilized to operate the equipment and/or view the operating parameters for the equipment.

In certain situations, for example in medical settings where the equipment is connected to a patient and the touch screen is required to operate the equipment and view the vital statistics of the patient as determined or measured by the equipment, when the touch screen is initially connected, i.e., when the patient is first connected to the equipment or when the screen is replaced due to damage or for some other reason, it is desired to have the touch screen up and running as quickly as possible. However, the process of locating the appropriate secondary device, connecting the secondary device to the touch screen or equipment, and then running the appropriate calibration program to configure the touch screen, which can require a restart of the touch screen and equipment to allow the calibration to become effective, can be time consuming in these types of situations.

In addition, in many situations it is required to stop or pause the normal operation of the touch screen device in order to enable the touch screen device to be calibrated. This can create issues in that when normal operation is ceased or paused, the monitoring function of the touch screen device is stopped, such that no information is being delivered to the individual about the item being monitored.

Therefore, it is desirable to provide an improved method or procedure of calibrating the touch screen either by itself or when connected to the equipment during an initial start-up of the touch screen in order to conduct a calibration of the touch screen for use in controlling the operation of and displaying the measurements of the equipment without the need for attachment of secondary devices to the touch screen or the equipment, without any restart of the touch screen and/or equipment, and optionally during the normal operation of the touch screen device, without shutting down the normal and ongoing functions of the touch screen device

BRIEF DESCRIPTION OF THE INVENTION

In the present invention a touch screen connected to a piece of equipment is configured with a calibration procedure that can be initiated directly through the touch screen by the operator performing a predetermined pattern of points of contact with the touch screen. The pattern is sensed by the screen and is used to initiate a request for confirmation of the intent to calibrate the touch screen, which can then be commenced with a repeated performance of the predetermined pattern of contact on the touch screen by the operator. The calibration procedure uses the pattern of points contact with the touch screen to calibrate the touch screen, as well as to initiate the procedure. The calibration procedure can be conducted at the initial start-up of the touch screen device or equipment to which the touch screen is connected, or at any time when the touch screen is replaced due to damage or other issues with the operation of the touch screen. The calibration procedure does not require any secondary devices to be connected to the touch screen or the equipment or a restart to apply the calibration to the touch screen, such that the calibration procedure can be conducted during the normal operation of the touch screen device without affecting the normal function of the touch screen device.

DETAILED DESCRIPTION OF THE INVENTION

Figure 1:
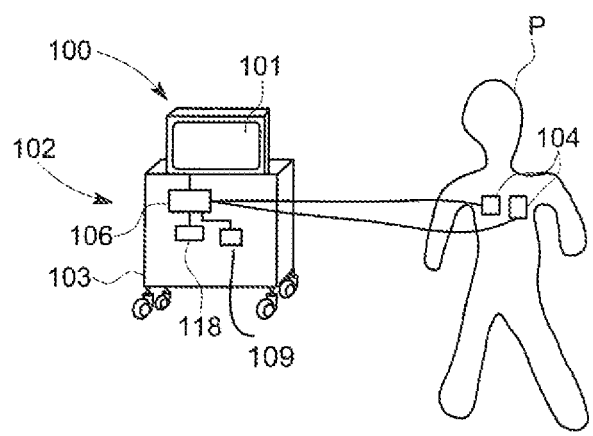
FIG. 1 is an isometric view of a touch screen operably connected to a piece of equipment to control the operation of and display the measurements of the equipment in accordance with an exemplary embodiment of the invention.

FIG. 1 illustrates an exemplary embodiment of the invention in which a touch screen display 100 is operably connected to a piece of monitoring equipment 102, which can be any suitable type of equipment that utilizes a touch screen display 100 for the operation of the equipment 102 in conjunction with the display of various operating parameters of the equipment 102 and/or of an object, machine, individual or other item operably connected to the equipment 102 for monitoring. The touch screen display 100 is formed as any suitable type of touch sensitive device in which points of contact of an individual with the surface or screen 101 of the display 100 create electrical signals that are sensed by the display 100 and associated with various functions for the display 100 ascribed to the particular points or areas of the screen 101.

In the exemplary embodiment of FIG. 1, the equipment 102 takes the form of a medical monitoring device 103 that has one or more sensors 104 operably connected in any suitable manner between the medical monitoring device 103 and a patient P in order to monitor and determine the status of various vital functions of the patient P. The medical monitoring device 103 includes a central processing unit (CPU) 106 operably connected to the sensors or leads 104 in order to receive data from the sensors 104 and compute various parameters of specified bodily functions of the patient P. These parameters can then be transmitted from the CPU 106 to the touch screen display 100 for presentation in a display section 107 of the display 100 to an individual monitoring the patient P via the touch screen display 100. The touch screen display 100 can also include certain controls 108 which can be selected by the individual in order to control and/or modify the operation of the medical monitoring device 103, as desired. The controls 108 are operated in a known manner by the individual contacting the touch screen display 100 at the points identified by the controls 108, which generates electrical signals sensed by the touch screen display 100. The signals generated at the particular point(s) of contact 105 sensed by the touch screen display 100 representing the points of contact 105 on the screen 101 can be utilized by the display 100 and/or the CPU 106 to determine what operations to perform using the medical monitoring device 103 based on the functions associated with the particular contact points 105 identified on the display 100.

The position of the display section 105 and the controls 108 on the display 100 is controlled by the operation of the CPU 106, such that the contact points on the display 100 remain constant during the operation of the medical monitoring device 103.

When the display 100 is first connected to the medical monitoring device 103, or when the display 100 is replaced, such as because of damage to or the miscalibration and/or inoperability of the display 100 to function properly for any reason, the display 100 must be properly calibrated with the CPU 106 in order to enable the display 100 to show the parameters in the display section 107 and to properly locate and sense the controls 108 for the operation of the medical monitoring device 103.

Figure 2:
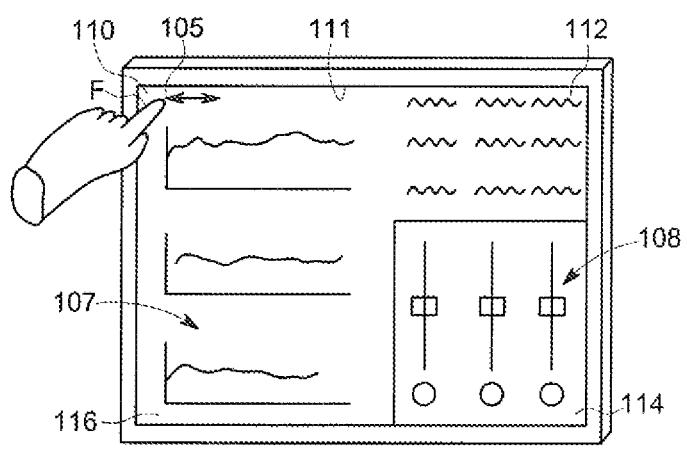
FIG. 2 is an isometric view of a hand of an operator initiating the calibration of the touch screen in accordance with an exemplary embodiment of the invention.
Figure 3:
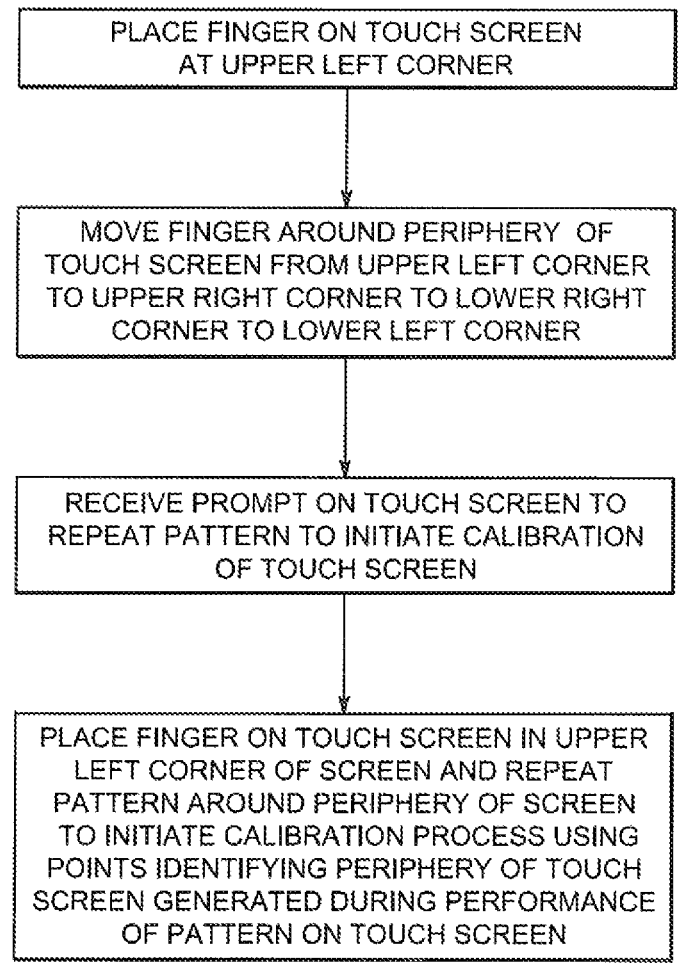
FIG. 3 is a schematic view of a flowchart of the calibration procedure performed using the touch screen in accordance with an exemplary embodiment of the invention.

To calibrate the display 100, as shown in the exemplary embodiment of FIG. 3, the display 100 is connected to the medical monitoring device 103 such that the contact signals generated by contact with the display 100 can be transmitted to the CPU 106 which can consequently recognize the points of contact on the display 100. Once connected, the individual performs the following steps:
1. individual puts a finger F on the display 100 in a specified start location or point of contact 105 with the screen 101, such as the left top corner 110 of the display 100; and
2. individual drags the finger F along the screen 101 of the display 100 in a specified calibration-initiating pattern, e.g., along the periphery 111 of the screen 101, i.e., from top left corner 110 to the top right corner 112, from the top right corner 112 to the bottom right corner 114, from bottom right corner 114 to the bottom left corner 116, and from the bottom left corner 116 back to the top left corner 110, as shown in the exemplary embodiment of FIG. 2.

During the completion of these steps, the signals generated by the points of contact 105 on the screen 101 of the display 100 are sensed and transmitted to the CPU 106. The CPU 106 then compares the pattern of the signals from the points of contact 105 with a calibration-initiating pattern stored in an electronic storage medium component or database 109 operably connected to the CPU 106 to determine if the pattern of contact with the display 100 is potentially a request for the initiation of the calibration procedure for the display 100. However, in order to confirm this request, the CPU 106 causes a prompt message to appear on the display 100 stating that the calibration-initiating pattern must be repeated in order for the calibration of the display 100 to begin, optionally along with a time period, e.g., ten (10) seconds, in which the repeated request must be made to begin the calibration of the display 100.

Upon viewing the prompt, the individual can then repeat the above steps, which generates the signals on the display 100 that indicate to the CPU 106 that the calibration process for the connected display 100 is to be initiated, which are again compared with the calibration-initiating pattern stored in an associated electronic storage medium in the touch screen display 100 or the medical monitoring device 103, such as a database 109. Additionally, the signals generated by the movement of the finger of the individual around the periphery 111 of the display 100 in one or both steps can be directly utilized to calibrate/configure the display 100 with the display section 105 and controls 108, in conjunction with the calibration procedure. In an exemplary embodiment of the invention, using this exemplary pattern of movement of the finger F of the individual around the periphery 111 of the display 100, the coordinate system of the display 100 is consequently determined and communicated to the CPU 106. The particular coordinate system for the display 100 as determined by the pattern can then be utilized by the software employed by the CPU 106 to configure the information displayed on the screen 101 even if the coordinate systems for various displays 100 are different, reversed and/or are not the same size.

Further, during normal operation of the touch screen 100 and equipment 103, the software driver 118 used by the CPU 106 to read the coordinates of the points of contact with the screen 101 can constantly monitor the screen 101 to determine if the calibration-initiating pattern has been generated and consequently initiate a calibration mode for the display 100.

In other exemplary embodiments, the calibration-initiating pattern of the contact points 105 required to initiate the calibration mode can be selected as desired, such as by having the individual contact the screen 101 at discrete contact points 105 located at each of the corners 110-116 of the screen 101, optionally in any particular and specified order. In addition, the calibration procedure of the display 100 can be initiated at any time during the use of the display 100, e.g., when additional sensors 104 are connected to the equipment 103 to monitor additional bodily function parameters of the patient P using the display 100. In this example, the pattern for initiating the calibration procedure can be performed on the display 100, and the CPU 106 can immediately calibrate and reconfigure the display 100 to illustrate the information to be shown on the screen 101 from the added sensors 104.

Further, the pattern of points of contact 105 can be utilized to initiate the calibration of touch screen displays 100 that are not connected to other equipment 102 as the pattern can be recognized by the internal processing units and databases (not shown) of the displays 100 and used to calibrate the display 100 directly. Additionally, the confirmation of the initiation of the calibration process can be done in a manner other than by repeating the initial calibration-initiating pattern, such as by forming a different confirmation pattern on the screen 101, which can be formed of a single point of contact 105, e.g., pressing a confirmation button icon (not shown) on the screen 101, or a number of sequential points of contact 105 as directed by the CPU 106.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A piece of equipment for monitoring and providing information about an item operably connected to the equipment, the piece of equipment comprising:
   a touch screen display having a screen configured to display the information about the item from the equipment and to control the operation of the equipment, the touch screen display capable of sensing points of contact between the screen and an individual operating the touch screen display;
   a central processing unit operably connected to the screen and configured to:
      receive signals from the screen regarding the points of contact on the screen;
      compare a pattern of the points of contact with a predefined calibration initiating pattern which is a pattern extending around the periphery of the screen, the predefined calibration initiating pattern defining calibration parameters for use in the calibration of the touch screen display; and
      in response to determining that the pattern of the points of contact matches the predefined calibration initiating pattern, cause the screen to display a prompt message requesting the individual to confirm initiation of calibration by repeating the predefined calibration initiating pattern.

2. The equipment of claim 1 wherein the central processing unit is operably connected to a database in which the predefined calibration initiating pattern is stored for comparison with the signals transmitted from the screen to the central processing unit.

3. The equipment of claim 1 further comprising a number of sensors adapted to be disposed on the item to be monitored and operably connected to the central processing unit.

4. A method for initiating a calibration of a touch screen display, the method comprising the steps of:
   providing the touch screen display with a screen configured to sense points of contact between the screen and an individual;
   providing a central processing unit and an electronic storage medium operably connected to one another and to the screen, and in which a calibration initiating pattern of points of contact with the screen is stored which is a pattern extending around the periphery of the screen, the calibration initiating pattern defining calibration parameters for use in the calibration of the touch screen display;
   comparing a first pattern of the points of contact with the calibration initiating pattern; and
   in response to determining that the first pattern of the points of contact matches the calibration initiating pattern, displaying on the screen a prompt message requesting the individual to confirm initiation of calibration by repeating the calibration initiating pattern.

5. The method of claim 4 further comprising:
   receiving a second pattern of points of contact as a confirmation of calibration; and
   calibrating the touch screen display.

6. The method of claim 5 wherein the second pattern matches the calibration initiating pattern.

7. The method of claim 4 wherein the first pattern of points of contact on the screen can be conducted at any time during the operation of the touch screen display.

8. A touch screen display comprising:
   a screen capable of sensing points of contact between the screen and an individual operating the screen and generating signals representing the points of contact with the screen;
   a central processing unit operably connected to the screen and configured to receive the signals from the screen regarding the points of contact on the touch screen display;
   a storage medium operably connected to the central processing unit and in which a calibration initiating pattern of points of user-initiated contact with the screen is stored which is a pattern extending around the periphery of the screen, the calibration initiating pattern defining calibration parameters for use in the calibration of the touch screen display,
   wherein the central processing unit is configured to:
      compare a first pattern of the points of contact with the calibration initiating pattern; and
      in response to determining that the first pattern of the points of contact matches the calibration initiating pattern, cause the screen to display a prompt message requesting the individual to confirm initiation of calibration by repeating the calibration initiating pattern.

9. The touch screen display of claim 8, wherein in the central processing unit is further configured to:
   receive a second pattern of points of contact as a confirmation of calibration; and
   calibrate the touch screen display.

10. The touch screen display of claim 8, wherein the calibration initiating pattern includes individual contacts at discrete points in a specified order.

* * * * *